United States Patent
Svojanovsky

(10) Patent No.: US 10,368,771 B2
(45) Date of Patent: Aug. 6, 2019

(54) EEG ELECTRODE AND MULTI-CHANNEL EEG ELECTRODE SYSTEM

(71) Applicant: Alexander Svojanovsky, Gilching (DE)

(72) Inventor: Alexander Svojanovsky, Gilching (DE)

(*) Notice: Subject to any disclaimer, the term of this patent is extended or adjusted under 35 U.S.C. 154(b) by 0 days.

(21) Appl. No.: 13/895,868

(22) Filed: May 16, 2013

(65) Prior Publication Data

US 2013/0261421 A1 Oct. 3, 2013

Related U.S. Application Data

(63) Continuation-in-part of application No. 12/899,796, filed on Oct. 7, 2010, now abandoned, which is a continuation-in-part of application No. 12/047,507, filed on Mar. 13, 2008, now abandoned.

(51) Int. Cl.
| | |
|---|---|
| A61B 5/0478 | (2006.01) |
| A61B 5/04 | (2006.01) |
| A61B 5/00 | (2006.01) |

(52) U.S. Cl.
CPC ........ *A61B 5/0478* (2013.01); *A61B 5/04004* (2013.01); *A61B 5/6843* (2013.01); *A61B 5/7221* (2013.01); *A61B 5/6803* (2013.01); *A61B 2560/0209* (2013.01); *A61B 2560/0276* (2013.01); *A61B 2562/0209* (2013.01)

(58) Field of Classification Search
CPC combination set(s) only.
See application file for complete search history.

(56) References Cited

U.S. PATENT DOCUMENTS

| | | | |
|---|---|---|---|
| 5,509,421 A | 4/1996 | Muller et al. | |
| 5,511,553 A * | 4/1996 | Segalowitz | A61B 5/0006 128/903 |
| 5,817,029 A | 10/1998 | Gevins et al. | |
| 6,289,238 B1 * | 9/2001 | Besson et al. | 600/509 |
| 2001/0044573 A1 * | 11/2001 | Manoli et al. | 600/383 |
| 2003/0109905 A1 * | 6/2003 | Mok | A61B 5/0002 607/60 |
| 2005/0107716 A1 * | 5/2005 | Eaton et al. | 600/544 |
| 2006/0115323 A1 * | 6/2006 | Coppeta et al. | 403/270 |
| 2006/0276702 A1 | 12/2006 | McGinnis | |
| 2007/0112277 A1 | 5/2007 | Fischer et al. | |
| 2007/0225611 A1 * | 9/2007 | Kumar | A61B 5/0006 600/523 |

(Continued)

FOREIGN PATENT DOCUMENTS

WO WO2007086448 A1 * 8/2007 ........... A61B 5/0424

OTHER PUBLICATIONS

Jasper, H.H., The ten twenty electrode system of the international federation; Electroencephalography and Clinical Neurophysiology 10, pp. 371-375, 1958.

*Primary Examiner* — Christian Jang
*Assistant Examiner* — Karen Toth
(74) *Attorney, Agent, or Firm* — Laurence A. Greenberg; Werner H. Stemer; Ralph E. Locher

(57) ABSTRACT

A device comprises an indicating unit configured to indicate information and a connecting unit configured to connect the indicating unit to an electrode operable to sense an EEG signal, such that the information is indicated at a position at which the electrode is placed. The electrode includes a circuit board and an indicating unit, such as an LED, encased in a water-proof housing.

7 Claims, 13 Drawing Sheets

(56) References Cited

U.S. PATENT DOCUMENTS

| | | |
|---|---|---|
| 2007/0238945 A1* | 10/2007 | Delic .................. A61B 5/0478 |
| | | 600/383 |
| 2007/0239059 A1* | 10/2007 | McIver ........................ 600/544 |
| 2007/0268065 A1 | 11/2007 | Cranford, Jr. et al. |
| 2008/0091089 A1* | 4/2008 | Guillory .............. A61B 5/0478 |
| | | 600/301 |
| 2008/0091090 A1 | 4/2008 | Guillory et al. |
| 2008/0119728 A1 | 5/2008 | Frenkel et al. |
| 2008/0146958 A1* | 6/2008 | Guillory et al. ............. 600/544 |
| 2008/0243020 A1 | 10/2008 | Chou |
| 2009/0012381 A1* | 1/2009 | Kuramori ............ A61B 5/0424 |
| | | 600/393 |
| 2009/0044113 A1 | 2/2009 | Jones et al. |
| 2009/0171166 A1 | 7/2009 | Amdundson et al. |
| 2010/0094107 A1 | 4/2010 | Lamego |
| 2011/0071416 A1 | 3/2011 | Terada et al. |
| 2011/0087129 A1 | 4/2011 | Chetham et al. |
| 2011/0102550 A1 | 5/2011 | Daniel et al. |
| 2011/0288447 A1 | 11/2011 | Cochran |
| 2012/0010491 A1 | 1/2012 | Rowlandson et al. |

\* cited by examiner

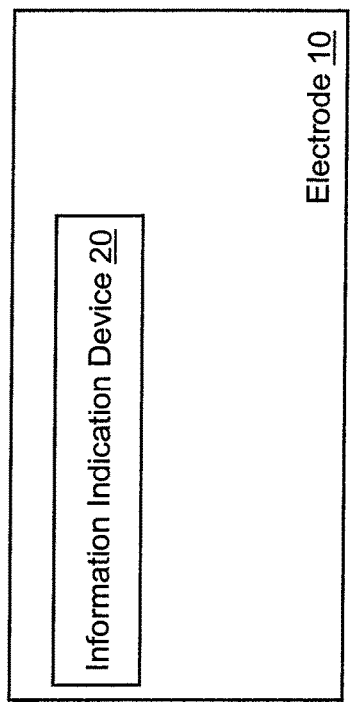
FIG. 4
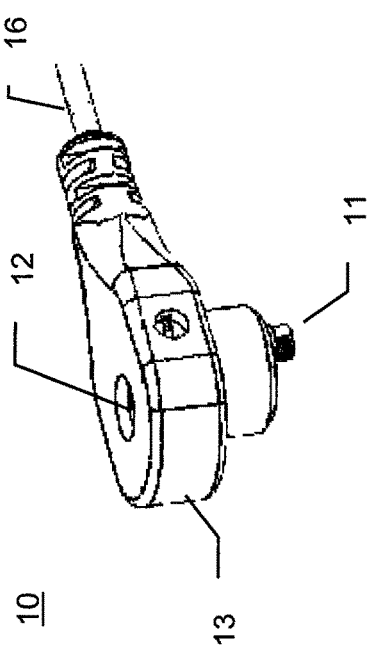
FIG. 3
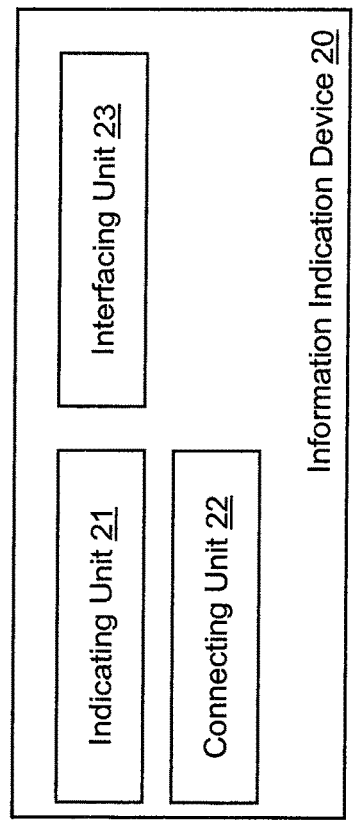
FIG. 6
FIG. 5

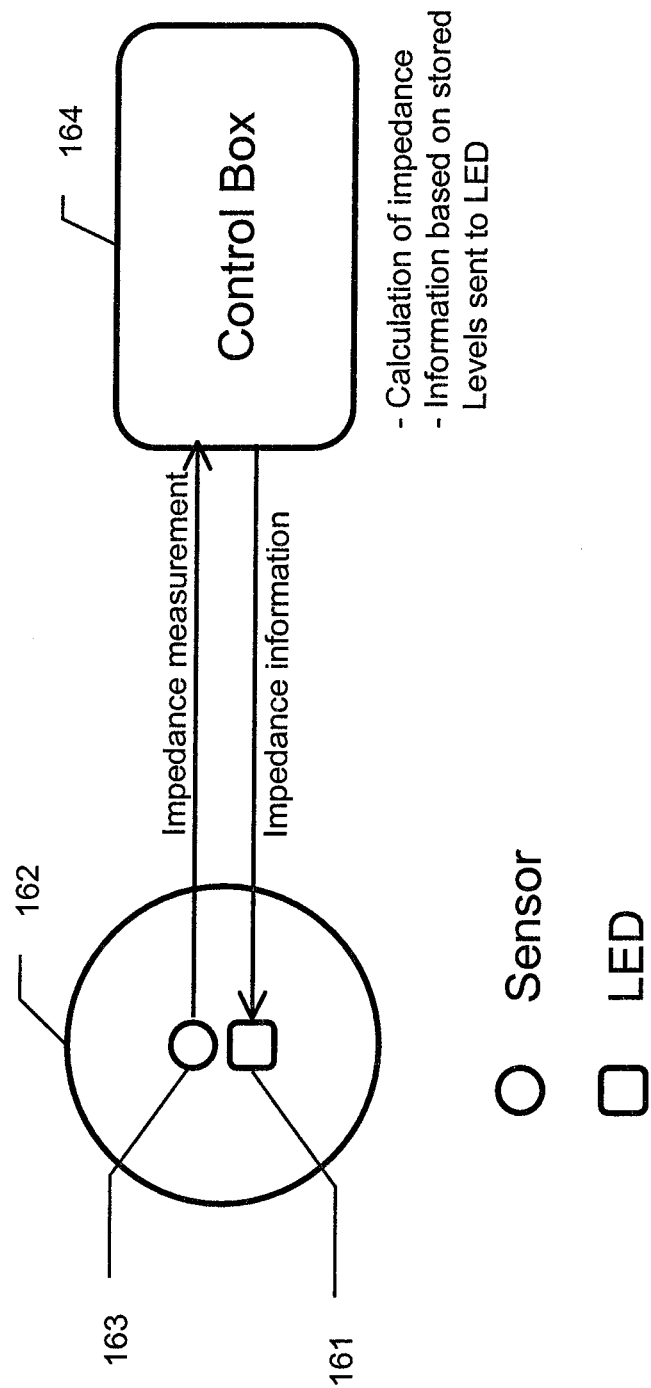

EEG ELECTRODE AND MULTI-CHANNEL EEG ELECTRODE SYSTEM

CROSS-REFERENCE TO RELATED APPLICATION

This application is a continuation-in-part of copending patent application Ser. No. 12/047,507, filed Mar. 13, 2008, and of copending patent application Ser. No. 12/899,796, filed Oct. 7, 2010; the copending applications are herewith incorporated by reference.

BACKGROUND OF THE INVENTION

Field of the Invention

The present invention relates to a multi-channel EEG electrode system. In particular, the invention relates to electrodes of such system, an information indication device for the electrodes and a position localizing system.

Electroencephalography is a neurophysiologic measurement of electrical activity of the brain by recording from electrodes placed on the scalp. The resulting traces are known as an electroencephalogram (EEG) and represent an electrical signal (postsynaptic potentials) from a large number of neurons. Electrical currents are not measured, but rather voltage differences between different parts of the brain.

In a conventional scalp EEG, recording is obtained by placing electrodes on the scalp with a conductive gel, usually after preparing the scalp area by light abrasion to reduce impedance. Some EEG systems use a fabric cap into which the electrodes are imbedded.

Moreover, EEG topography is a neuroimaging technique in which a large number of EEG electrodes are placed onto the head, following a geometrical array of evenly spaced points. A special software plots the impedance of electrodes (electrical conductance) on a computer screen or printer, by coding the values in several tones of color. The spatial points lying between electrodes are calculated by mathematical techniques of interpolation (calculating intermediary values on the basis on the value of its neighbors), and thus a smooth gradation of colors is achieved.

BRIEF SUMMARY OF THE INVENTION

It is accordingly an object of the invention to provide a multi-channel EEG electrode system which overcomes various disadvantages of the heretofore-known devices and methods of this general type and which further improves the prior art devices and methods.

With the foregoing and other objects in view there is provided, in accordance with the invention, an electrode operable to sense an EEG signal, comprising:
 a circuit board;
 a pin connected to the circuit board;
 an indicating unit configured to indicate information; and
 a casing enclosing said circuit board and said indicating unit in a water-proof manner and enabling the information to be provided outside of said casing, said casing having a cylindrical hole passing therethrough, said hole being configured to receive an agent and to direct the agent to said pin.

In a preferred embodiment of the invention, the electrode has a connecting unit configured to detachably connect the electrode to a plug connector.

In accordance with a another feature of the invention, the indicating unit includes, or is, an LED and the casing is (at least partially) translucent, or even transparent, enabling the LED to be visually observed from outside the casing.

In accordance with an added feature of the invention, the electrode further comprises:
 an interfacing unit configured to interface said indicating unit with an external apparatus;
 wherein said indicating unit is configured to receive instructions from the external apparatus and display the information based on the instructions.

In the preferred embodiment, the information displayed by the indicating unit is visual information that is different from the EEG signal.

It is further preferred for the indicating unit to be is mounted on a circuit board and directly on top of a portion of the electrode effective to sense the EEG signal.

With the foregoing and other objects in view there is also provided, in accordance with the invention, a display device that comprises:
 an indicating unit configured to indicate information; and
 a connecting unit configured to connect the indicating unit to an electrode operable to sense an EEG signal;
 wherein the information is indicated at a position at which the electrode is placed.

In accordance with an added feature of the invention, the electrode has a circuit board and the connecting unit is configured to connect the indicating unit to the circuit board of the electrode.

In accordance with an added feature of the invention, the electrode has a casing and the connecting unit is configured to connect the indicating unit to the casing of the electrode.

In accordance with an added feature of the invention, the display device further comprises an interfacing unit configured to interface the indicating unit with an external apparatus, and the indicating unit is configured to receive instructions from the external apparatus and indicate the information based on the instructions.

In accordance with an added feature of the invention, the indicating unit is configured to indicate the information based on measurement signals output by the electrode. In accordance with a preferred embodiment of the invention, the measurement signals represent impedance measurement results from an impedance measurement. Preferably, the measurement signals represent EEG measurement results.

In accordance with again an added feature of the invention, the information is visual display information, audio information, vibration information, and/or radio information.

With the above and other objects in view there is also provided, in accordance with the invention, a plug connector, comprising:
 a plurality of plug connection units each configured to detachably connect to a connecting unit of an electrode; and
 a multiplexing unit configured to receive input signals from the plurality of plug connection units, and to multiplex the input signals into an output signal.

With the above and other objects in view there is also provided, in accordance with the invention, a system, comprising:
 a plurality of electrodes operable to sense an EEG signal, the electrodes being arranged in a three-dimensional pattern and each including an indicating unit configured to display information at a position at which the respective the electrode is placed;
 an image sensing device configured to acquire stereoscopic images of the plurality of electrodes;
 a control device configured to sequentially cause the indicating unit of each electrode to display the information and simultaneously cause the image sensing device to acquire the stereoscopic image of the respective the electrode; and a processing device configured to calculate position information of each electrode of the plurality of electrodes from the stereoscopic images.

With the above and other objects in view there is also provided, in accordance with the invention, a system, comprising:

a plurality of electrodes operable to sense an EEG signal, the electrodes being arranged in a three-dimensional pattern and each including an indicating unit configured to transmit information at a position at which the electrode is placed;

a sensing device configured to acquire the information;

a control device configured to sequentially cause the indicating unit of each electrode to transmit the information and simultaneously cause the sensing device to acquire the information; and a processing device configured to calculate position information of each electrode of the plurality of electrodes from the information.

Once more in sum: The invention provides for a device that indicates information on measurement results derived by using an EEG electrode in a manner such that a testing person can easily be provided with this information. Further, there is provided a water-proof EEG electrode. According to an additional embodiment of the invention, there is provided a system that localizes positions of electrodes placed, say, on a head without requiring intervention of a testing person. In accordance with another embodiment, there is provided a plug connector that enables easy replacement of a damaged electrode.

Other features which are considered as characteristic for the invention are set forth in the appended claims.

Although the invention is illustrated and described herein as embodied in multi-channel EEG electrode system, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE SEVERAL VIEWS OF THE DRAWING

FIG. 3 shows an exterior view of the electrode operable to sense an EEG signal according to an embodiment of the invention;

FIG. 4 shows a schematic block diagram of the electrode according to an embodiment of the invention;

FIG. 5 shows a schematic block diagram illustrating an information indication device according to an embodiment of the invention;

FIG. 6 shows a plan view of an internal structure of the electrode according to an embodiment of the invention;

FIG. 17 shows a schematic diagram illustrating an EEG system according to an embodiment of the invention.

DETAILED DESCRIPTION OF THE INVENTION

Figure 1:
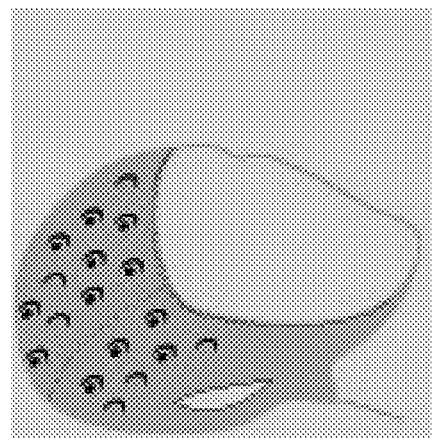
FIG. 1 is a schematic diagram illustrating an electrode cap worn by a test person.

According to an embodiment of the invention, active electrodes are used in a multi-channel EEG electrode system for measuring electrical activity of the brain. Referring now to the figures of the drawing in detail and first, particularly, to FIG. 1 thereof, the electrodes may be inserted in a cap worn by a test person as shown in the figure, or attached separately to the subject's head, whose electrical activity of the brain is to be measured.

An active electrode may comprise circuitry for adapting an input impedance of, say, 200 MOhm or more to an impedance working range of, say, 1 to 120 kOhm. By decreasing the output electrode impedance motion artifacts and interferences from external sources such as power lines, etc. are reduced, which results in a higher signal-to-noise ratio.

Figure 2:
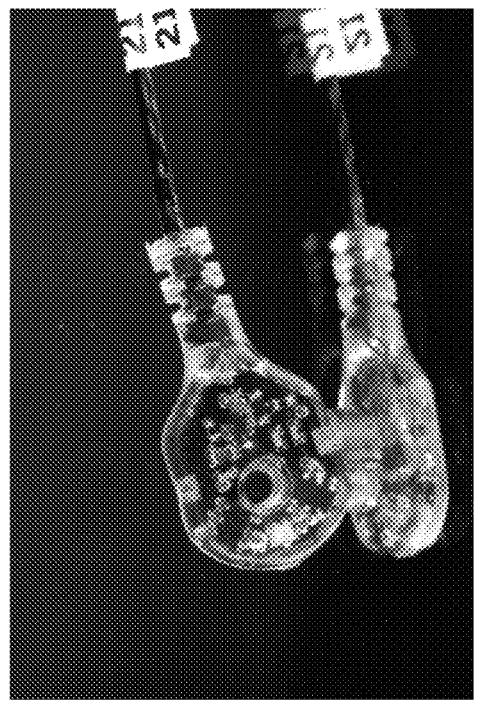
FIG. 2 are perspective views of an electrode operable to sense an EEG signal according to an embodiment of the invention.

An electrode 10 according to an embodiment of the invention is shown in FIGS. 2 and 3. FIG. 2 show top and side/bottom views of the electrode 10, and FIG. 3 shows a more schematic exterior view of the electrode 10 comprising a pin 11 which contacts with a scalp and a hole 12 for inserting an agent such as a conductive gel in order to provide contact between the scalp and the pin 11. Circuitry of the electrode 10 is included in a casing 13.

The electrode 10 may comprise an information indication device 20 as schematically shown in FIG. 4. According to an embodiment of the invention, as schematically shown in FIG. 5, the device 20 comprises an indicating unit 21 for indicating information, a connecting unit 22 and an interfacing unit 23. The connecting unit 22 may connect the indicating unit 21 to the electrode 10 such that the information is indicated at a position at which the electrode 10 is placed. The device 20 may comprise a display device such as a Light Emitting Diode (LED), a Liquid Crystal Device (LCD), etc., or an output device outputting audio signals or vibration signals, or a combination thereof. According to an embodiment, the signals output by the device 20 are receivable by a testing person.

It is to be noted that the arrangement of the functional blocks of the device 20 is not construed to limit the invention.

According to an embodiment of the invention, the connecting unit 22 connects the indicating unit 21 to a circuit board 14 of the electrode 10 schematically shown in FIG. 6.

Alternatively, the connecting unit 22 connects the indicating unit 21 to the casing 13 of the electrode 10. In this case, commercial electrodes may be used and attached to a subject's head, which have the indicating unit 21 according to the invention attached. A commercial EEG software may calculate impedance values. According to an embodiment of the invention, based on the calculated impedance values instructions are provided to the indicating unit 21 using a control unit 832 as described below in connection with FIG. 9. The indicating unit 21 may be connected to the (commercial) electrode in a permanent manner such that it is not required to remove the indicating unit 21 from the electrode for cleaning, for example.

Figure 9:
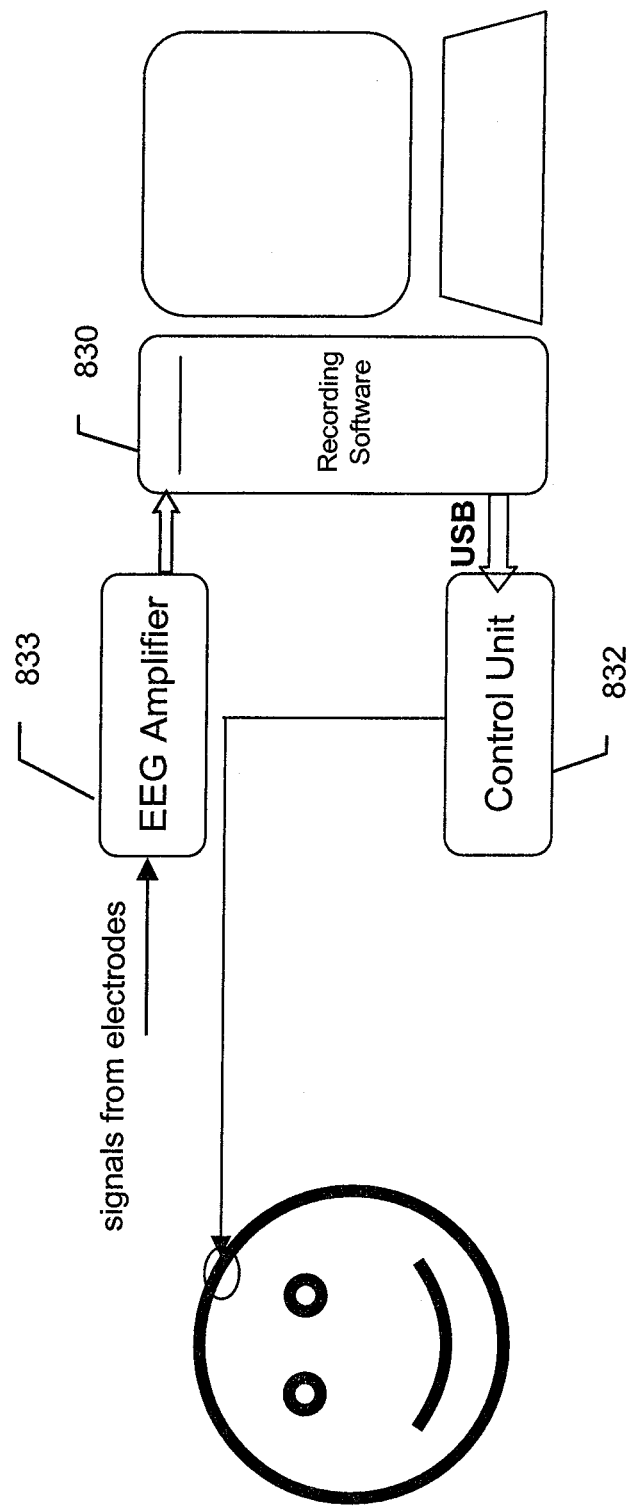
FIG. 9 shows a schematic block diagram illustrating an EEG system according to an embodiment of the invention.

The interfacing unit 23 may interface the indicating unit 21 with an external apparatus 830 shown in FIG. 9, such as a Personal Computer, Workstation, etc. The interfacing unit 23 may comprise a Universal Serial Bus (USB). The interfacing unit may also comprise the control unit 832 as shown in FIG. 9.

Figure 16:
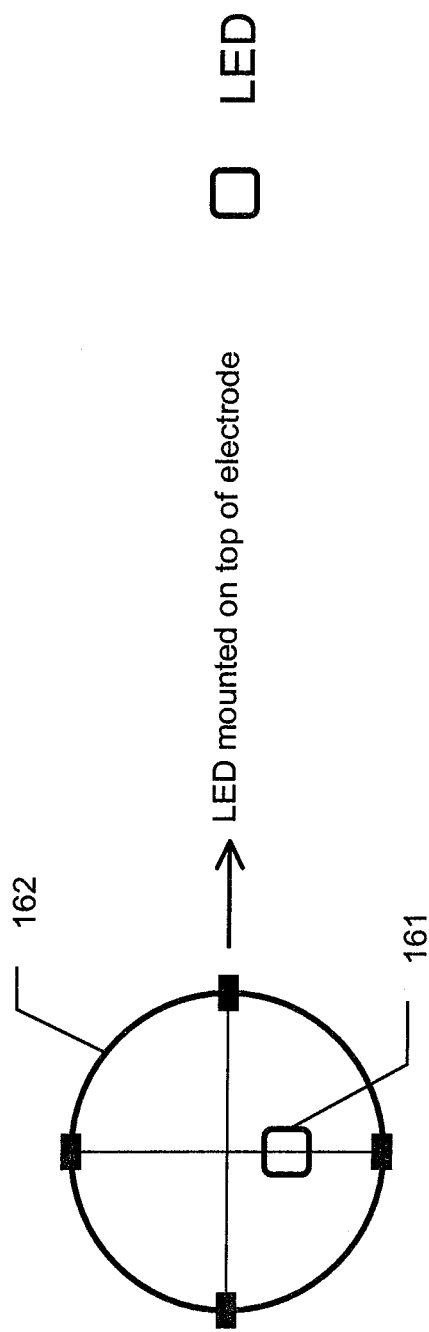
FIG. 16 shows a schematic diagram illustrating an EEG system according to an embodiment of the invention.

FIG. 16 shows a schematic diagram illustrating an EEG system according to an embodiment of the invention, in which an LED 161 serving as indicating unit is mounted on top of an electrode 162. Here, the expression "on top of" means that the indicating unit is disposed opposite from the effective surface of the electrode. In its functional position on top of a head, therefore, the LED is placed radially outward and radially away from the skull. Preferably, the LED 161 is placed directly on top of the electrode so as to efficiently and unambiguously indicate its location relative to the electrode. The LED receives impedance information from a control box (not shown in FIG. 16) which in turn may receive the impedance information from a PC (not shown in FIG. 16). The LED 161 illuminates in accordance with the impedance information.

FIG. 17 shows a schematic diagram illustrating an EEG system according to an embodiment of the invention, in which an LED 171 serving as indicating unit is provided in an electrode 172 together with a sensor 173 which is involved in impedance measurement. A control box 174 calculates impedance based on the impedance measurement results from the sensor 173 and transmits impedance information based on stored levels (to be described below) to the LED 171. The LED 171 illuminates in accordance with the impedance information.

Figure 8:
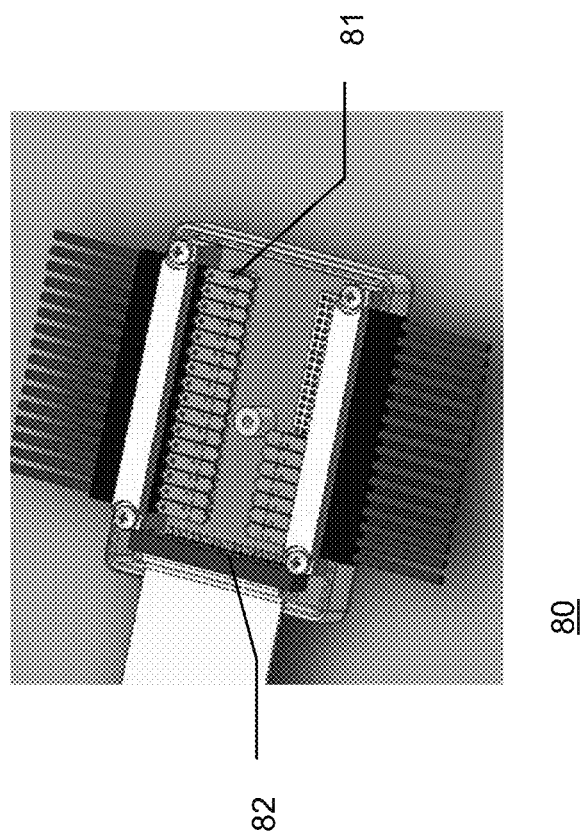
FIG. 8 shows a plug connector according to an embodiment of the invention.

As shown in FIG. 3, the electrode 10 may further comprise a connecting unit 16, such as a cable having three lines and a shielding, for detachably connecting the electrode 10 to a plug connector 80 as shown in FIG. 8. The plug connector 80 comprises a plurality of plug connection units 81 each detachably connecting to a connecting unit 16 of an electrode 10, and a multiplexing unit 82 which receives input signals, i.e. EEG signals, from the plurality of plug connection units 81, and multiplexes the input signals received into an output signal.

Figure 7:
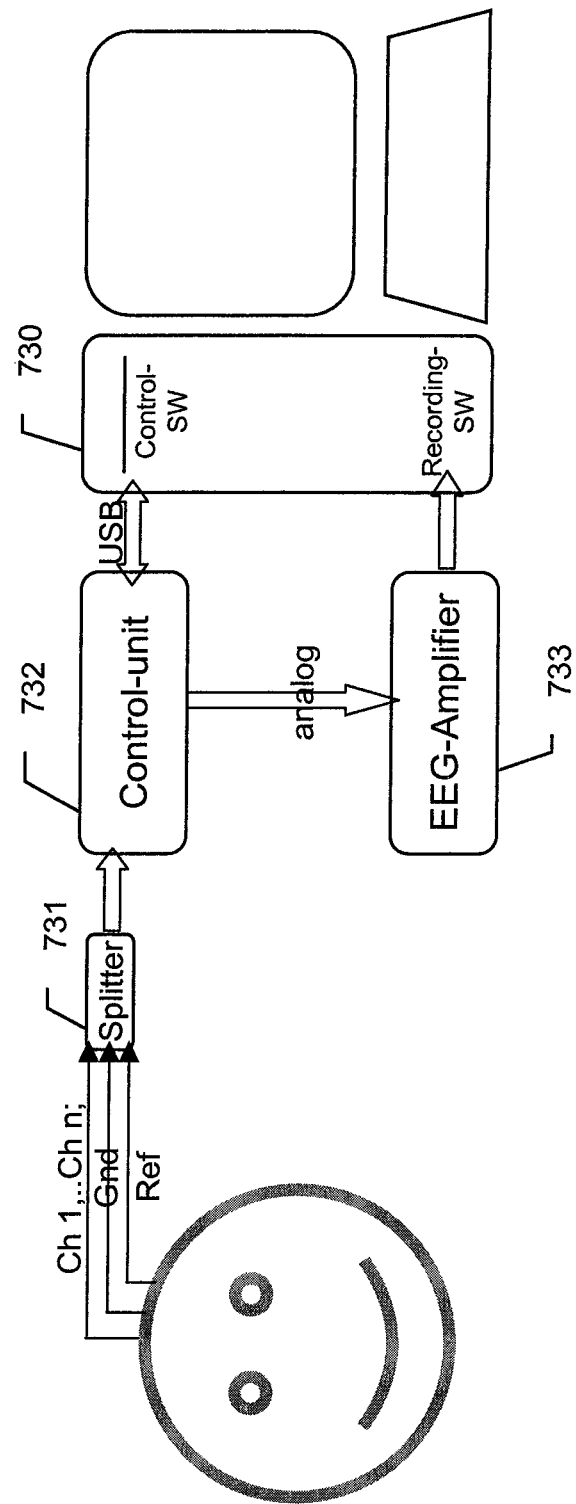
FIG. 7 shows a schematic block diagram illustrating an EEG system according to an embodiment of the invention.

As shown in FIG. 7, the splitter 731 acting as plug connector 80 receives signals from electrodes or channels Ch1 . . . Chn as well as Gnd and Ref signals from ground and reference electrodes. The splitter comprises a chip (multiplexing unit 82) which multiplexes the received signals or lines onto an output unit such as a ribbon cable as shown in FIG. 8, comprising lines which are fewer in number than the received lines.

With the plug connector 80 shown in FIG. 8, the electrodes 10 can be detachably connected to plug connection units 81. Thus, a damaged electrode can be replaced in an easy manner.

As shown in FIG. 7, from the splitter 731 the multiplexed lines or signals are fed to a control unit 732 which outputs analogue signals to an EEG amplifier 733 which converts the analogue signals to digital data which are fed to a control and recording entity 730 which may act as the external apparatus.

The control and recording entity 730 and the control unit 732 may be connected via a USB line for controlling and/or powering the control unit 732. The USB line shown in FIG. 8 may act as interfacing unit 23. The EEG amplifier 733 may be connected to the control and recording entity 730 via an optical waveguide.

The indicating unit 21 may receive instructions from an external apparatus and indicate the information based on these instructions.

FIG. 9 shows a system according to an embodiment of the invention in which the indicating unit 21 receives instructions from a recording entity 830 via a control unit 832 which is connected via USB with the recording entity 830. The recording entity 830 outputs the instructions based on signals provided by an EEG amplifier 833. In other words, the recording entity 830 comprises a software for calculating impedance values from signals provided by the EEG amplifier 833 which will be described in greater detail below. Based on the calculated impedance values instructions are calculated and, using the USB connection and the control unit 832, provided to the indicating unit 21. The instructions may be provided from the control unit 832 to the indicating unit 21 using a wireline or a wireless connection.

It is also possible to calculate the impedance values in the control unit 832.

Alternatively or in addition, the indicating unit 21 may indicate the information based on measurement results provided by the electrode 10. The measurement results comprise impedance measurement results from an impedance measurement to be described by referring to FIG. 13. In other words, the electrode 10 may comprise a circuit for calculating the impedance values inside the electrode and the indicating unit 21 may indicate the information based on the calculated impedance values without feedback from the control unit 832.

Alternatively or in addition, the measurement results comprise EEG measurement results.

FIG. 6 shows a plan view of an internal structure of the electrode 10 according to an embodiment of the invention. As shown in FIG. 6, the electrode 10 comprises the circuit board 14, the indicating unit 21, and the hole 12 which in this embodiment passes through the circuit board 14. However, it is to be noted that the invention is not limited to an arrangement in which the hole 12 passes through the circuit board 14.

The casing 13 shown in FIG. 3 may enclose the circuit board 14 and the indicating unit 21 in a water-proof manner and such that the information is provided to the outside of the casing 13. For example, in case the indicating unit 21 is connected to the circuit board 14 and comprises a display unit providing display signals, the casing 13 should be translucent or transparent, at least in part. The hole 12 passing through the casing 13 is of cylindrical shape in order ensure watertightness of the electrode 10. When forming the casing 13 to enclose the circuit board 14, e.g. by casting, the circuit board 14 may be dislocated although it is held in a holder during the casting. By using the cylindrical shape of the hole 12 the casing 13 can be formed to completely enclose the circuit board 14.

Figure 10:
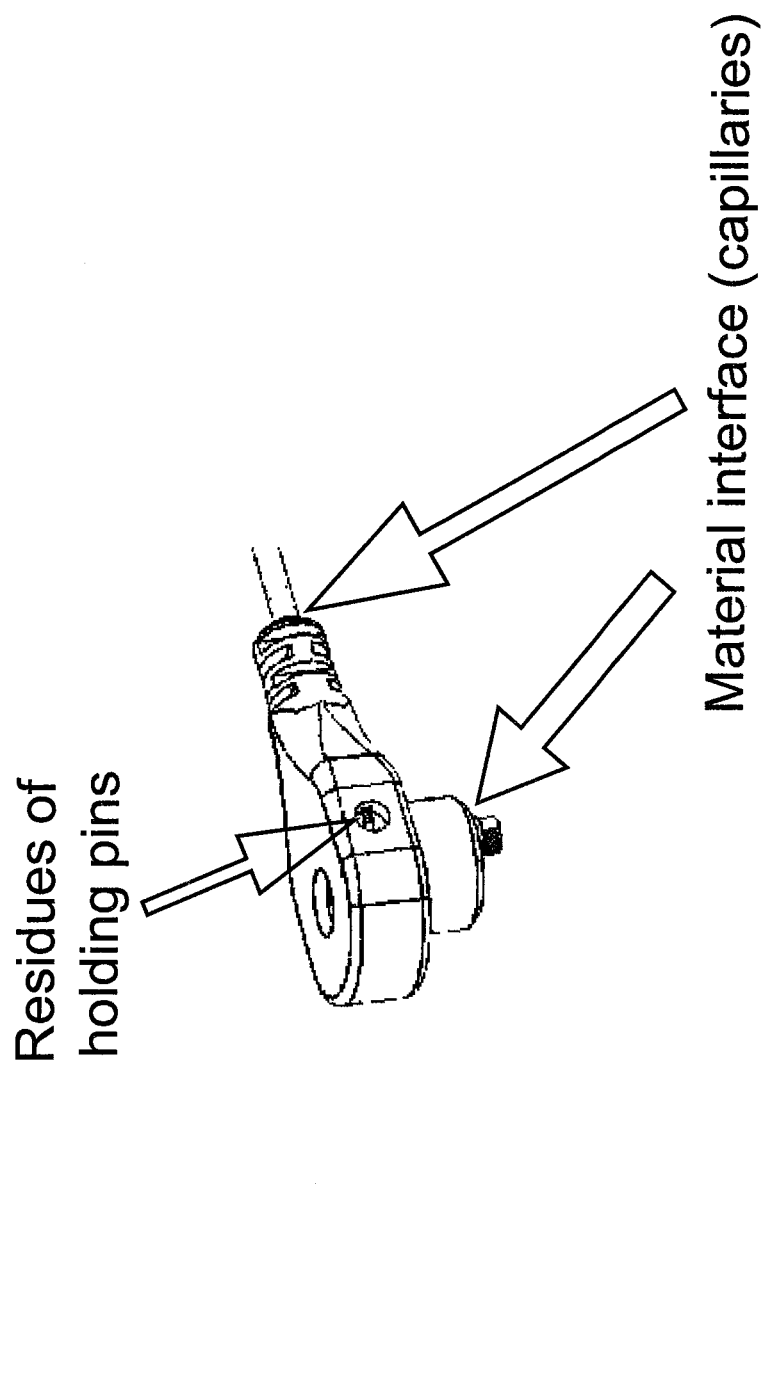
FIG. 10 shows weak spots of an electrode.

FIG. 10 shows weak spots of the EEG electrode 10 which may result from forming the casing 13. In addition to the hole as described above, weak spots may be present at residues of holding pins used during casting, and at material interfaces e.g. between the pin 11 and the cable 16 and the material used for casting. For avoiding the weak spots, according to an embodiment of the invention a melt casting technique is used for forming the casing, in which polyurethane is used which is generated in a mold by polyaddition.

Figure 11:
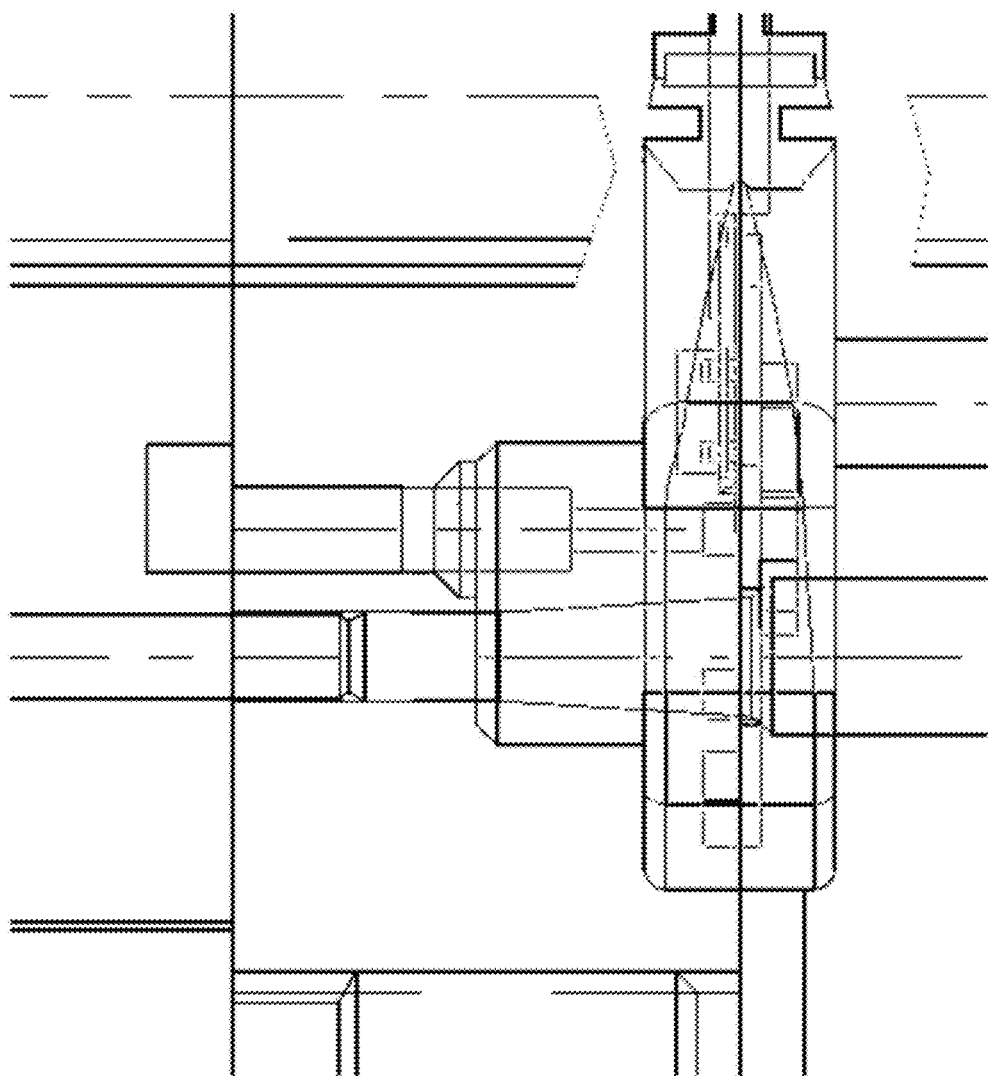
FIG. 11 shows a mold including an electrode for melt casting.

FIG. 11 shows a schematic view of the casing of the electrode formed inside the mold. In the melt casting technique adopted according to an embodiment of the invention, two plastic materials are poured into the mold made of tempered steel, in which circuit boards as schematically shown in FIG. 6 have been inserted. For example, eight circuit boards may be inserted in one mold. After the plastic materials were poured into the mold, the plastic materials are cured inside the mold so that the polyurethane formed by polyaddition of the plastic materials encloses each of the circuit boards in a watertight manner. With the melt casting technique the casting material can be processed without requiring pressure. Moreover, the casting material compounds with the material of the electrode in a better way than done in die casting. In addition, with the melt casting no holding pins are necessary and no air bubbles are generated. Thus, the weak spots shown in FIG. 10 can be avoided.

Figure 12:
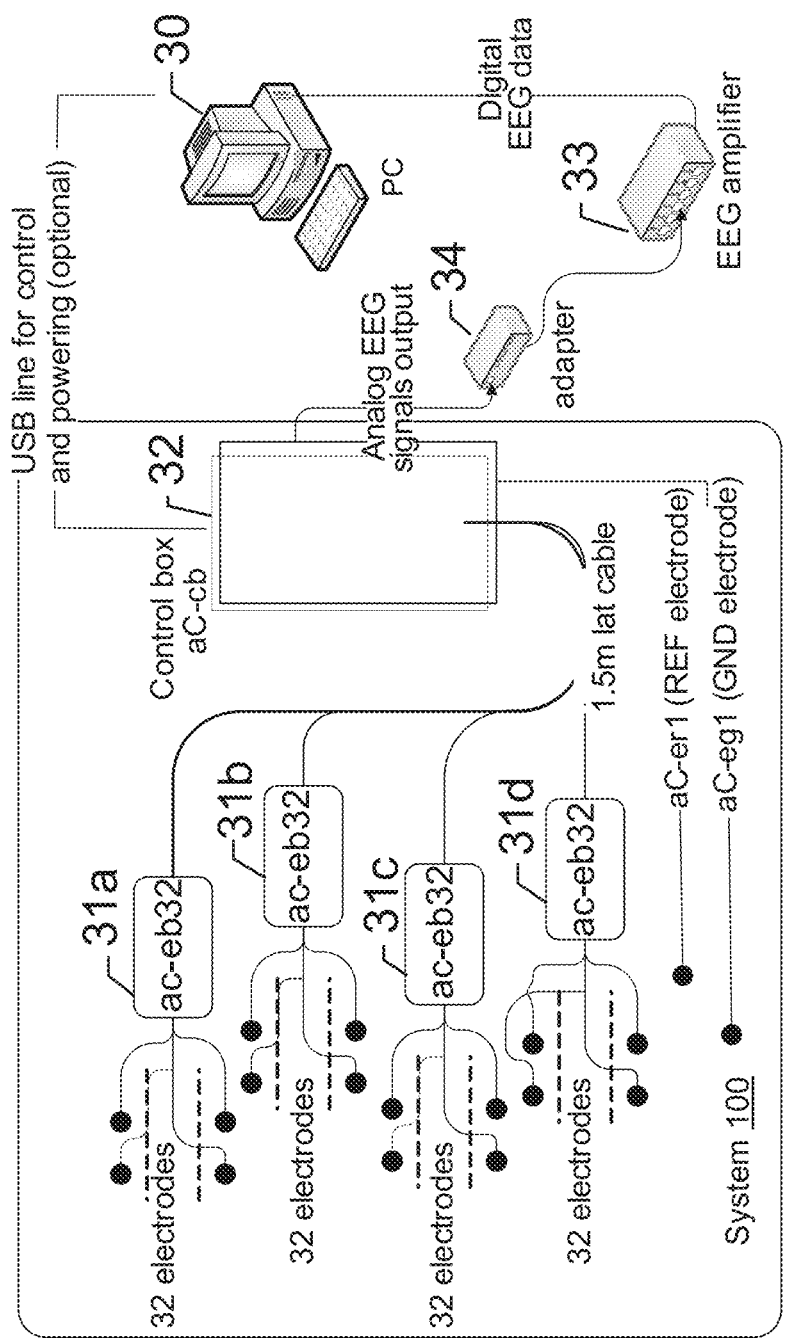
FIG. 12 shows a schematic block diagram illustrating an 128-channel EEG system.

FIG. 12 shows a schematic block diagram illustrating a 128-channel EEG system 100. In this system 100 four 32 channels active electrodes blocks 31*a*, 31*b*, 31*c* and 31*d* are shown. To each block 31*a*-31*d* 32 electrodes are connected. The system 100 further comprises an active reference (REF) electrode aC-er1 with e.g. a 2 m cable, a ground (GND) electrode aC-eg1 with e.g. a 2 m cable, and a 128 channels control box 32. The electrodes each may be formed by the electrode 10 described above.

The blocks 31-*a*-31*d* are connected to the control box 32 using 1.5 m cables, for example. The electrodes aC-er1 and aC-eg1 are also connected to the control box 32 using the 2 m cables. The control box 32 receives EEG signal sensed by the 128 electrodes and outputs analogue EEG signals to an EEG amplifier 33 which converts the analogue EEG signals to digital EEG data which are fed to a PC 30 which may act as the external apparatus. The analogue EEG signals may be guided through an adapter 34 before entering the EEG amplifier 33, where they are converted into signals which can be processed by the EEG amplifier 33.

The PC 30 and the control box 32 may be connected via a USB line for controlling and/or powering the control box 32. The USB line shown in FIG. 5 may act as interfacing unit 23.

The system 100 may comprise the following operation modes: sleep mode, acquisition mode, which can be performed in combination with an active shielding sub-mode, impedance measurement mode, and test signal mode.

The sleep mode is equivalent to a system off-state. In this mode the system 100 is waiting for a turn-on command from the PC 30 or can be activated by pressing a "Power" button.

The system 100 is going to the acquisition mode after turn-on. In this mode the system 100 transfers the signals from the electrodes 10 attached to a subject head to the external EEG amplifier 33. The following table shows parameter values of the system 100 for the acquisition mode according to an embodiment of the invention.

| Parameter | Value |
| --- | --- |
| Amplification | 1 |
| Tolerance of amplification | <0.001% |
| Differential and common input impedance | >200 MOhm |
| Pass band | 0-5000 Hz |
| Self noise (include sensors' noise) | <2 µV p.p. for 0.1-35 Hz band |
| Dynamic range | ±1000 mV |
| Self offset | <20 mV (including sensors' offset) measured in 0.9% saline |

In the active shielding sub-mode, inverted and gained voltage from the REF electrode aC-er1 is injected to the GND electrode aC-eg1 for common-mode noise compensation. In some cases this strongly decreases the common-mode voltage for an external EEG amplifier.

According to an embodiment of the invention, the impedance measurement mode can be selected from the acquisition mode, not directly from the sleep mode. Impedance is measured independently for each electrode, including REF and GND electrodes, by using a time separated method of current injection.

Figure 13:
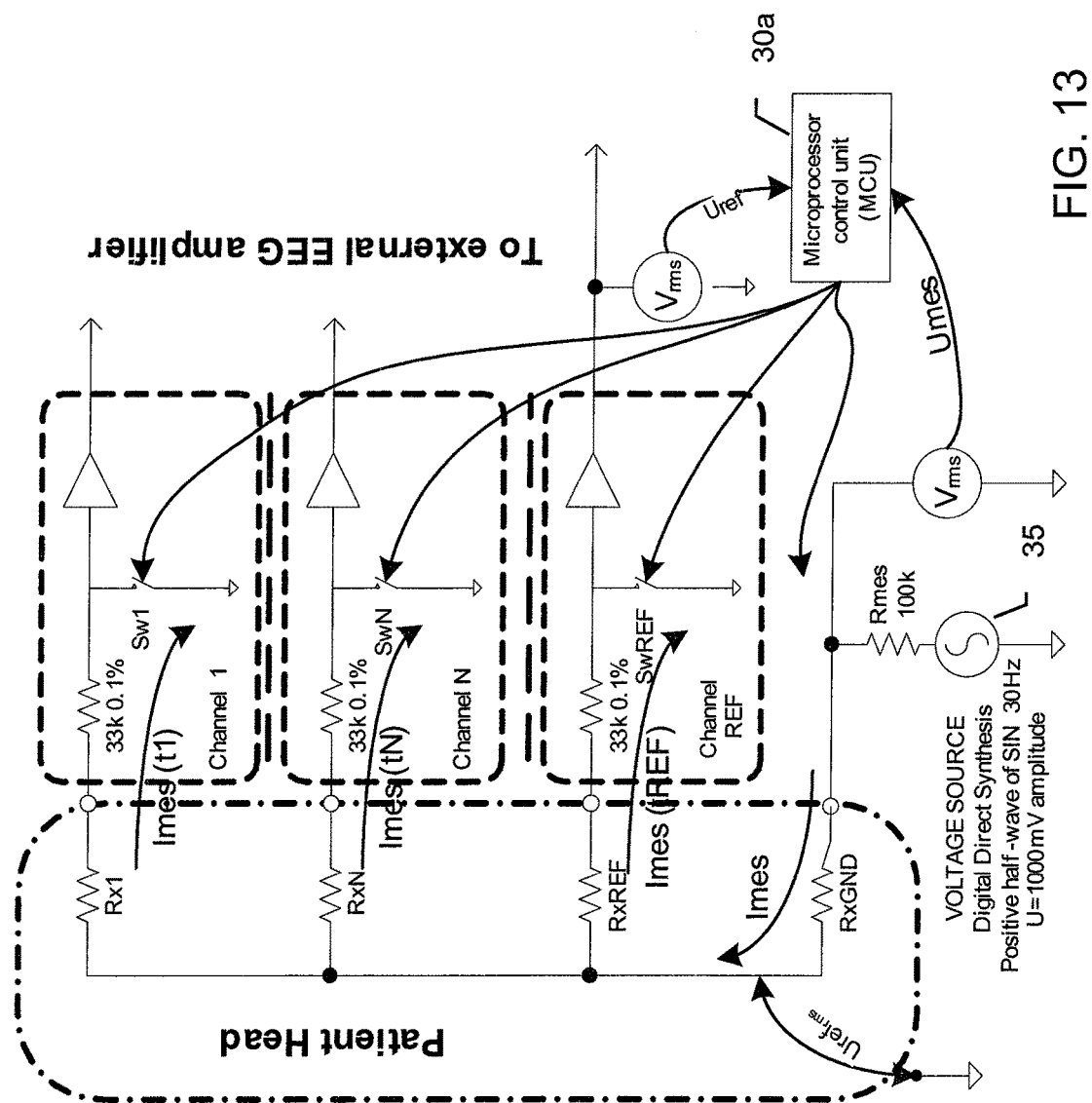
FIG. 13 shows a schematic diagram illustrating impedance measurement.

FIG. 13 shows a schematic diagram illustrating the impedance measurement. In FIG. 6 a channel 1 corresponding to an electrode $10_1$, a channel N corresponding to an electrode $10_N$, and a channel REF corresponding to the reference electrode aC-er1 are illustrated. It is to be understood that similar channels are provided also for electrodes $10_2$ to $10_{N-1}$ of the N-channel EEG system. In the system 100 shown in FIG. 12 128 channels or electrodes $10_1$-$10_{128}$ are provided.

Each channel shown in FIG. 13 comprises a measuring impedance circuit which includes a 33 kOhm resistor for limiting a patient auxiliary current. The 33 kOhm resistor is a parasitic resistor for the measuring impedance circuit. Moreover, each channel comprises a switch SW controlled by an MCU 30*a*. The MCU 30*a* may be part of the PC 30 shown in FIG. 12.

Before measuring is started, the ground electrode aC-eg1 is connected.

In a first step, the MCU 30*a* closes an electronic switch SW1 of channel 1 or electrode $10_1$, so that current from the ground electrode aC-eg1 will flow at this electrode only, as all another channels have high input impedance.

In a second step the MCU 30*a* causes a voltage source 35 to generate $V_{sin}$=1V amplitude ($U_{sin\_rms}$=0.7$V_{rms}$) positive half-wave of SIN 30 Hz by Digital Direct Synthesis and inject current via an $R_{mes}$ resistor from the ground electrode aC-eg1 to a bioimpedance object (patient head).

At this moment, in a third step, the MCU 30*a* measures a voltage $U_{mes}$ on the load (Rx1+RxGND+33 kOhm) and $U_{ref}$ on the reference electrode REF (as high impedance input). Then, in a fourth step the MCU 30*a* opens the electronic switch SW1 and in a fifth step calculates Rx1'=$U_{mes}$/(($U_{sin\_rms}$-$U_{mes}$)/$R_{mes}$).

If the electrode $10_1$ of channel 1 and the REF electrode are connected (Rx1' and RxREF' are in valid range from 33 kOhm-15% to 153 kOhm+15%), RxGND'1 is calculated by the MCU 30*a* in a sixth step:

RxGND'1=Rx1'-($U_{ref}$/(($U_{sin\_rms}$-$U_{mes}$)/$R_{mes}$)).

In a seventh step, the MCU 30*a* waits for 2-4 msec.

The above-described steps 1-7 are repeated for all N channels and the REF electrode.

After steps 1-7 have been performed for all N channels and the REF electrode, the MCU 30*a* calculates RxGND=Sum (RxGND'1 . . . RxGND'N)/N, where N is the number of connected electrodes $10_1$-$10_N$. Then, the MCU 30a calculates Rx1 . . . RxN as Rx=RxN'-RxGND-33 kOhm.

The following table shows parameter values for the impedance measurement according to an embodiment of the invention:

| Parameter | Value |
| --- | --- |
| Impedance measurement frequency | 30 Hz |
| Range | 0 to 120 kOhm |
| absolute tolerance | <±15% (in 1 to 120 kOhm range) |
| Injected current | <7.5 µA |
| Time of measuring cycle | <4 sec. for 128 channels |

According to an embodiment of the invention, the indicating unit 21 comprises LEDs which are connected to the circuit board of each of the electrodes $10_1$-$10_N$, or are attached to the casing of each of the electrodes $10_1$-$10_N$. During the above-described impedance measurement the impedance values may be read via a USB-port by the external apparatus 30 and shown by illuminating the LEDs with different colors depending on measured values. After turn-on of the system 100 the default threshold levels and corresponding colors may be set by default to:

Green Color—impedance less than 10 kOhm
Yellow Color—impedance 10-50 kOhm
Red Color—impedance greater than 50 kOhm According to an embodiment of the invention, these thresholds can be set by a command from the PC 30. This setting may be stored into a nonvolatile memory. The LEDs may also be disabled by the PC 30.

Illumination of the LEDs may be performed based on a command from the PC 30, i.e. the PC 30 causes illumination of an LED of a corresponding electrode 10 with a specific color depending on the measured impedance of the corresponding electrode 10. Alternatively, it is also possible to have an illumination control circuit in the electrode 10, which causes the LED to illuminate in the specific color. The impedance values and corresponding color of each electrode 10 can be stored in the PC 30 for further processing.

The duration of the impedance measuring mode may be limited to 3 min. After this time-out the system 100 should switch to the acquisition mode. This duration can be changed by a command from the PC 30 and stored in the nonvolatile memory.

In the test signal generation mode a meander signal of 200 µV±2% amplitude and 1 sec duration is applied between the ground electrode aC-eg1 and each electrode $10_1$-$10_N$.

This mode may be used for testing the functionality of the system 100, checking the system connection to the external EEG amplifier 33 and for testing/calibration of the external EEG amplifier 33. For this purpose it is necessary to short-connect all electrodes by water immersion and set a monopolar acquisition scheme in the external EEG amplifier 33.

By using the indicating unit 21 in connection with each electrode 10 of the system 100, a testing person can easily recognize which electrode 10 has which impedance value, and is not required to search for the electrode on the patient's head by referring to a screen only on which the patient's head with the electrodes attached may be schematically displayed.

Moreover, the indicating unit 21, e.g. the LEDs, may be driven by the external apparatus 30 in reaction to EEG signals acquired in the acquisition mode in order to indicate regions in the patient's head where the EEG signals have been generated.

Information indication by the indicating unit 21 using LEDs is not restricted to different colors. It is also possible to cause blinking of the LEDs with different frequencies depending on the impedance values measured by the respective electrodes. The indicating unit 21 also comprises any kind of display device including an LCD, a plasma display, etc.

As described above, the indicating unit 21 also is not restricted to displaying information. The indicating unit 21 may comprise any kind of output device which outputs signals which can—by a test person or a testing person—be associated with a position at which the signals are output.

Moreover, the indicating unit 21 comprises any kind of output device which outputs signals which can be recognized by an image sensing device. The image sensing device may comprise a digital camera.

Figure 14:
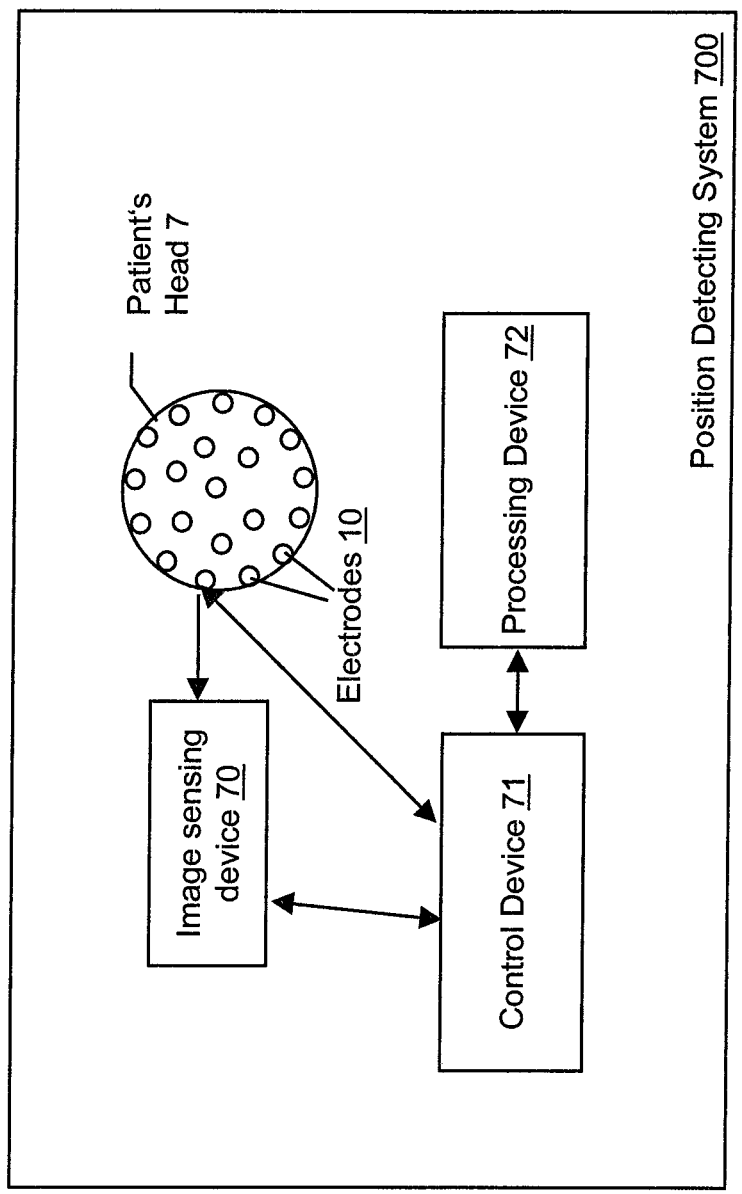
FIG. 14 shows a schematic block diagram illustrating a position detecting system according to an embodiment of the invention.

According to a further embodiment of the invention, position of the electrodes of the system 100 is detected using a position detecting system 700 as shown in FIG. 14. The system 700 may comprise a plurality of electrodes 10 operable to sense an EEG signal, arranged in a three-dimensional pattern and each comprising the indicating unit 21 which, according to this embodiment, displays information at a position at which the electrode is placed. The plurality of electrodes 10 may be positioned on a patient's head 7. The system 700 further comprises an image sensing device 70 which acquires stereoscopic images of the plurality of electrodes 10, a control device 71 which sequentially causes the indicating unit 21 of each one of the plurality of electrodes 10 to display the information and simultaneously cause the image sensing device 70 to acquire the stereoscopic images of each one of the plurality of electrodes 10, and a processing device 72 which calculates position information of each one of the plurality of electrodes 10 from the stereoscopic images.

It is to be noted that the arrangement of the functional blocks of the system 700 is not construed to limit the invention. For example, the functions of the control device 71 and the processing device 72 can be included in one apparatus. Moreover, the control device may be formed by the external apparatus 30.

After acquiring the position information for each electrode 10, the processing device 72 may compare the position information with reference position information and decide whether the acquired position information deviates. In case the acquired position information deviates, the electrode concerned may be re-positioned. Alternatively, the deviation is taken into account when electrodes measuring brain activity and locations of the activity in the brain are correlated.

According to an embodiment of the invention, the image sensing device 70 may comprise two or more cameras for taking two or more stereoscopic images from different positions. In case of fixed cameras it is preferred that four cameras are used to be able to take three images of each of the electrodes positioned over the patient's head 7 at different positions.

According to an alternative embodiment, the image sensing device 70 comprises one camera which is placed at different positions for taking the stereoscopic images.

The processing device 72 recognizes the information displayed by the indicating unit 21 in each stereoscopic image and identifies it as common point. A line of sight (or ray) can be constructed from the camera location to this common point. It is the intersection of these rays (triangulation) that determines the three-dimensional location of the common point and, thus, the position of the electrode whose indicating unit 21 displays the information. More sophisticated algorithms can exploit other information about the scene that is known a priori, for example symmetries, in some cases allowing reconstructions of 3D coordinates from only one camera position.

The position detection system 700 can be used with electrodes 10 comprising the indicating unit 21 inside or with electrodes 10 having the indicating unit 21 fixed to the casing after manufacture of the electrode.

Figure 15:
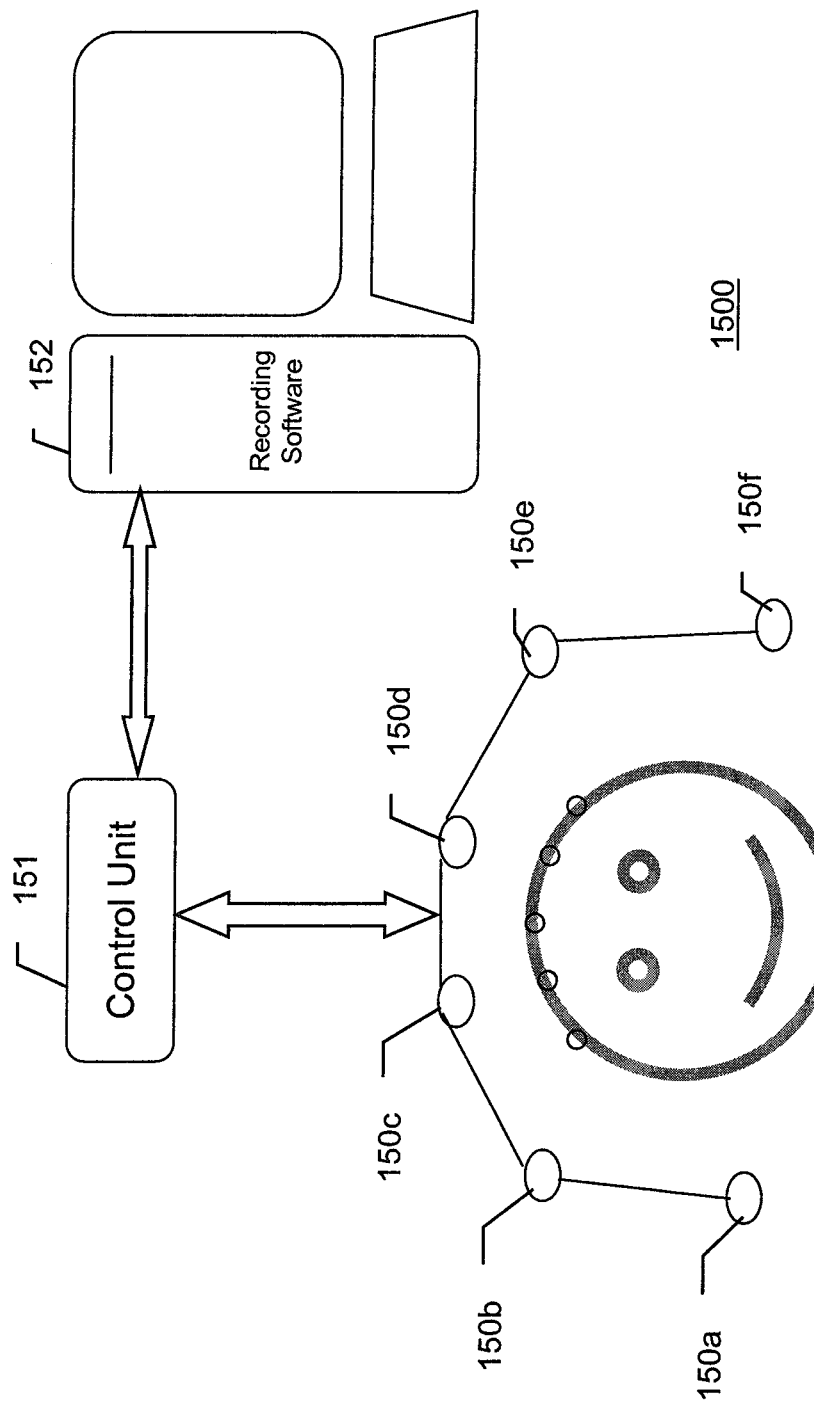
FIG. 15 shows a schematic block diagram illustrating a position detecting system according to an embodiment of the invention.

FIG. 15 shows a position detection system 1500 according to an embodiment of the invention.

The system 1500 comprises six video cameras 150a-150f which are mounted on a rotatable and vertically adjustable stand (not shown). Calibration is performed using a calibration cube by means of software for adjusting position of the video cameras. After calibration, only common movement of the video cameras 150a-150f is allowed.

The video cameras 150a-150f are arranged such that at least two of the video cameras 150a-150f sense an electrode positioned at any position on a head. This is achieved by arranging the video cameras 150a-150f on the stand. The head has attached a plurality of electrodes, each comprising an LED as indicating unit 21. For a photogrammetric survey each electrode on the head (the electrodes are shown as small circles on the head in FIG. 15) is driven using a control unit 151 and a recording entity 152. Driving an electrode means that the LED of this electrode is turned on to illuminate.

At first, four reference electrodes are surveyed. After survey of the four reference electrodes, these are kept in an on-state, i.e. in an illumination state. Thus, the head may be moved without impacting the result of the further survey.

The video cameras 150a-150f are synchronized e.g. using a cable. The video cameras 150a-150f simultaneously pick up images of a driven electrode from different perspectives and fed the images via the control unit 151 to the recording entity 152. Each electrode is driven about 300 ms.

After conduction of the survey of all of the electrodes, which may be done automatically, position data of the electrodes are converted to a standardized sphere model using a least mean square fitting algorithm in order to obtain a scaling of the position data. The conversion may take place in the recording entity 152. The result may be exported into an ASCII file and fed to some analysing programs performing e.g. source localization.

According to an alternative embodiment of the invention, position of an electrode on the head may be measured using GPS. In this case, the indicating unit of the electrode may be a sender transmitting radio signals.

It is to be understood that the above description of the embodiments of the invention is illustrative of the invention and is not to be construed as limiting the invention. Various modifications and applications may occur to those skilled in the art without departing from the true spirit and scope of the invention as defined by the appended claims.

The invention claimed is:

1. An electrode operable to sense an electroencephalogram (EEG) signal, comprising:
    a circuit board;
    a pin connected to the circuit board;
    an indicating unit configured to display information, said indicating unit including an LED; and
    a casing enclosing said circuit board and said indicating unit in a water-proof manner and enabling the information to be provided outside of said casing, said casing having a cylindrical hole passing therethrough, said hole being configured to receive an agent and to direct the agent to said pin, said casing being at least partially translucent enabling said LED to be visually observed from outside said casing;
    said indicating unit mounted on said circuit board; and
    said indicating unit mounted on the electrode at a location disposed directly opposite a portion of the electrode effective to sense the EEG signal.

2. The electrode according to claim 1, comprising a connecting unit configured to detachably connect the electrode to a plug connector.

3. The electrode according to claim 1, further comprising:
    an interfacing unit configured to interface said indicating unit with an external apparatus;
    wherein said indicating unit is configured to receive instructions from the external apparatus and display the information based on the instructions.

4. The electrode according to claim 1, wherein said indicating unit further is configured to also output at least one of audio information, vibration information and radio information.

5. The electrode according to claim 1, wherein the information displayed by said indicating unit is visual information that is different from the EEG signal.

6. An electrode assembly for sensing EEG signals, comprising a plurality of electrodes according to claim 1, each being operable to sense an EEG signal and each having an indicating unit encased in a water-proof casing.

7. The electrode according to claim 1, wherein said indicating unit includes a plurality of LEDs with different colors, said plurality of LEDs are associated with different ranges of measured impedance values, and said LED is one of said plurality of LEDs.

* * * * *